US00PP10501P

Jnited States Patent [19]

erwer

[11] Patent Number: Plant 10,501

[45] Date of Patent: Jul. 14, 1998

4] DAHLIA PLANT NAMED 'GALLERY SALVADOR'

5] Inventor: Aad Verwer, Lisse, Netherlands

3] Assignee: Gebr. Verwer, Lisse, Netherlands

1] Appl. No.: 815,871

2] Filed: Mar. 12, 1997

1] Int. Cl.[6] ..... A01H 5/00

2] U.S. Cl. ..... Plt./87.8

8] Field of Search ..... Plt./87.8

6] References Cited

PUBLICATIONS

ITTM UPOVROM Listing for 'Gallery Salvador' as per 3R DHL0061(NL) Mar. 16, 1996.

*Primary Examiner*—James R. Feyrer

*Assistant Examiner*—Kent L. Bell

*Attorney, Agent, or Firm*—C. A. Whealy

[57] ABSTRACT

A distinct cultivar of Dahlia plant named 'Gallery Salvador', characterized by its suitability for potted plants, garden or patio plants, or as cut flowers; upright and spreading, compact and freely branching plant habit; medium green foliage; early and profuse flowering; rapid growth rate; large decorative-type inflorescences that are about 12 cm in diameter; light pink-colored ray florets; and good postproduction longevity.

1 Drawing Sheet

The present invention relates to a new and distinct cultivar Dahlia plant, botanically known as Dahlia hybrid and ferred to by the cultivar name 'Gallery Salvador'.

The new cultivar is a product of a planned breeding ogram conducted by the inventor in Lisse, The Nether- nds. The objective of the breeding program is to create mpact Dahlia cultivars that flower early and profusely ith desirable ray floret color and good post-production ngevity.

The new cultivar originated from a cross made by the ventor in the summer of 1992, of the nonpatented com- ercial cultivar 'Oriental Dream' as the female, or seed, rent with the nonpatented commercial cultivar 'Tout à Toi' the male, or pollen, parent. Compared to plants of the rent cultivars, the new Dahlia is more compact, more ely branching and inflorescences have a different ray ret color.

The cultivar 'Gallery Salvador' was discovered and lected by the inventor as a flowering plant within the ogeny of the stated cross in a controlled environment in sse, The Netherlands, in 1992. The selection of this plant s based on its compact and freely branching habit, unique y floret color, floriferousness and good postproduction ngevity.

Asexual reproduction of the new cultivar by terminal ttings taken in a controlled environment in Lisse, The etherlands, has shown that the unique features of this new hlia are stable and reproduced true to type in successive nerations.

The cultivar 'Gallery Salvador' has not been observed der all possible environmental conditions. The phenotype ay vary somewhat with variations in environment such as nperature, daylength and light intensity, without, how- er, any variance in genotype.

The following traits have been repeatedly observed and e determined to be the unique characteristics of 'Gallery lvador'. These characteristics in combination distinguish allery Salvador' as a new and distinct cultivar:

1. Suitable for potted plants, garden or patio plants, or as t flowers.
2. Upright and spreading, compact and freely branching ant habit.
3. Medium green foliage.
4. Early and profuse flowering.

5. Rapid growth rate.
6. Large decorative-type inflorescences that are about 12 cm in diameter.
7. Light pink-colored ray florets.
8. Good postproduction longevity with open inflores- cences maintaining good substance and color for about 14 days and plants maintaining good substance and flowering for 3 to 4 months.

The accompanying photograph illustrates the overall appearance of the new cultivar. The colored photograph comprises a side perspective view of a typical flowering plant of 'Gallery Salvador'. This photograph shows the colors as true as it is reasonably possible to obtain in colored reproductions of this type. Floret and foliage colors in the photograph may differ from the actual colors due to light reflectance.

In the following description, color references are made to The Royal Horticultural Society Colour Chart except where general terms of ordinary dictionary significance are used. The following observations and measurements describe plants grown in Lisse, The Netherlands, under conditions which approximate those generally used in commercial potted Dahlia production with day temperatures averaging 21° C. and night temperatures averaging 14° C. Plants were grown during the summer and measurements and numerical values were averages derived from typical flowering plants in September.

Botanical classification: Dahlia hybrid cultivar 'Gallery Sal- vador'.

Commercial classification: Decorative potted Dahlia.

Parentage:

*Male or pollen parent.*—Dahlia hybrid cultivar 'Tout à Toi' (not patented).

*Female or seed parent.*—Dahlia hybrid cultivar 'Ori- ental Dream' (not patented).

Propagation:

*Type.*—Terminal tip cuttings or by tuberous divisions.

*Time to rooting.*—About 14 days with soil temperatures of 20° C.

*Rooting habit.*—Central root with numerous secondary roots that are fine and fibrous.

Plant description:

*Appearance.*—Perennial herbaceous decorative-type Dahlia, suitable as potted plants, garden or patio plants, or as cut flowers. Upright and spreading, compact habit and freely branching.

*Plant height.*—About 25 cm, appropriate for 12 to 15-cm containers.

*Growth rate.*—Rapid, typically only 65 days are required from an unrooted cutting to a finished flowering plant.

*Foliage description.*—Leaf arrangement: Opposite, simple or compound. Compound leaves have either three or five leaflets. Leaf size, single: Length: About 7 cm. Width: About 6 cm. Leaf size, compound: Length: About 13 cm. Width: About 10 cm. Leaf shape: Ovate. Leaf apex: Acute. Leaf base: Acute. Leaf margin: Serrate. Leaf texture: Smooth. Color: Young foliage adaxial surface: 143A. Young foliage abaxial surface: 146D. Mature foliage adaxial surface: 137A. Mature foliage abaxial surface: 146B. Venation adaxial surface: 146C. Venation abaxial surface: 146C. Petiole: Length: 3 to 5 cm. Color: 146C.

Inflorescence description:

*Apperance.*—Fully double decorative-type inflorescence form with light pink-colored ray florets. Inflorescences borne on terminals above foliage.

*Flowering response.*—Under natural conditions, plant flower from July to November in the Northern Hemisphere.

*Postproduction longevity.*—On the plant, open inflorescences will maintain good color and substance for at about 14 days. As a cut flower, open inflorescences will maintain good color and substance for at least 7 days. Plants will continue to maintain good substance and flowering for three to four months.

*Quantity of inflorescences.*—Numerous, continuous flowering.

*Inflorescence size.*—Diameter: About 12 cm. Depth (height): About 3 cm.

*Inflorescence bud.*—Size: Length: About 8 mm. Width: About 10 mm. Rate of opening: About 20 days. Color: 151A.

*Ray florets.*—Shape: Long and narrow. Size: Length: About 5.5 cm. Width: About 1.6 cm. Apex: Obtuse. Margin: Entire. Texture: Smooth, satiny. Aspect: Flat. Color: When opening: 58A. Abaxial surface: 58D with 58A at margin. Adaxial surface: 58D with 58A at margin. Fading: Towards light pink to white.

*Disc florets.*—Few and inconspicuous.

*Peduncle.*—Length: 9 to 17 cm. Aspect: Strong, erect. Texture: Glabrous. Color: 146D.

*Sepals.*—Quantity: About 9. Shape: Ovate with pointed apex. Color: Abaxial surface: 144A. Adaxial surface: 144A.

*Reproductive organs.*—Androecium: Anther shape: Tubular and pointed. Anther length: Less than 1 mm Anther color: 17A. Pollen color: 13A. Gynoecium: Stigma color: 13A. Style length: About 6 mm. Style color: 150B.

Disease resistance: No known Dahlia diseases observed to date on plants grown under commercial conditions.

Seed production: Seed production has not been observed.

It is claimed:

1. A new and distinct cultivar of Dahlia plant named 'Gallery Salvador', as illustrated and described.

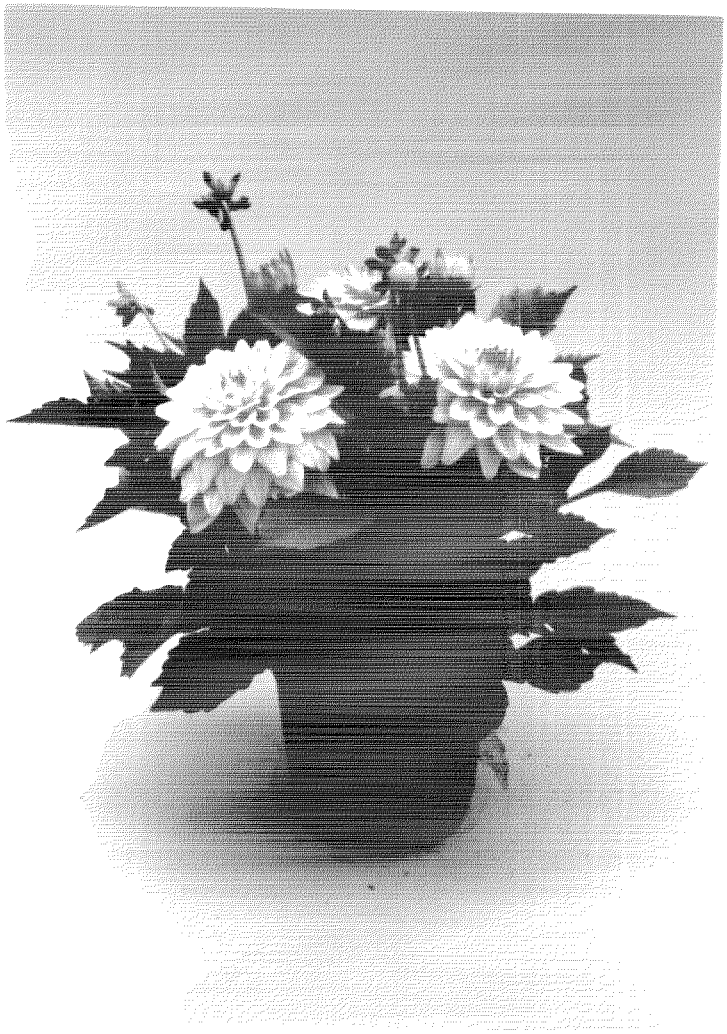

* * * * *